(12) United States Patent
Zheng et al.

(10) Patent No.: US 11,883,355 B2
(45) Date of Patent: Jan. 30, 2024

(54) METHOD AND DEVICE FOR LOCATING A HUMAN TARGET USING SUPERFICIAL VENOUS CHARACTERISTICS

(71) Applicant: SUZHOU KELING MEDICALTECHNOLOGY CO., LTD., Jiangsu (CN)

(72) Inventors: Yang Zheng, Suzhou (CN); Xing Zheng, Suzhou (CN)

(73) Assignee: SUZHOU KELING MEDICAL TECHNOLOGY CO., LTD., Suzhou (CN)

( * ) Notice: Subject to any disclaimer, the term of this patent is extended or adjusted under 35 U.S.C. 154(b) by 899 days.

(21) Appl. No.: 16/954,136

(22) PCT Filed: Dec. 14, 2018

(86) PCT No.: PCT/CN2018/121226
§ 371 (c)(1),
(2) Date: Jun. 15, 2020

(87) PCT Pub. No.: WO2019/114824
PCT Pub. Date: Jun. 20, 2019

(65) Prior Publication Data
US 2021/0161761 A1    Jun. 3, 2021

(30) Foreign Application Priority Data

Dec. 15, 2017    (CN) .......................... 201711346243.0
Dec. 15, 2017    (CN) .......................... 201711414612.5

(51) Int. Cl.
*G16H 50/50*    (2018.01)
*A61H 39/08*    (2006.01)
(Continued)

(52) U.S. Cl.
CPC ............ *A61H 39/02* (2013.01); *A61H 39/08* (2013.01); *G16H 50/50* (2018.01); *A61B 5/489* (2013.01); *A61H 2201/5043* (2013.01)

(58) Field of Classification Search
None
See application file for complete search history.

(56) References Cited

U.S. PATENT DOCUMENTS

2009/0326381 A1* 12/2009 Yuan ..................... A61B 5/015
                                                         600/473
2017/0156982 A1*  6/2017 Oda ....................... G16H 20/40
(Continued)

FOREIGN PATENT DOCUMENTS

CN          101166467 A     4/2008
CN          202136564 U     2/2012
(Continued)

OTHER PUBLICATIONS

International Search Report for PCT/CN2018/121226, dated Mar. 14, 2019.
Office Action issued for CN201711414612.5.

*Primary Examiner* — Idowu O Osifade
(74) *Attorney, Agent, or Firm* — True Shepherd LLC; Andrew C. Cheng

(57) ABSTRACT

Provided is a method for locating a human target using superficial vein characteristics, which includes acquiring a model displaying both of the human target and superficial veins; projecting the model on a body surface where the superficial veins are located, so that a ratio of a projection on the body surface to actual dimensions of a human body is (0.9-1.1):1; and adjusting a position of the projection of the model, observing the superficial veins, and making at least two of the superficial veins coincide with veins in the projection of the model, and determining that a position of (Continued)

the human target in the projection of the model is a projection of the human target on the actual body surface.

20 Claims, 9 Drawing Sheets

(51) Int. Cl.
*A61H 39/02* (2006.01)
*A61B 5/00* (2006.01)

(56) References Cited

U.S. PATENT DOCUMENTS

2019/0343717 A1* 11/2019 Yim ..................... A61B 5/004
2021/0000687 A1* 1/2021 Greiner ............. A61N 1/36175

FOREIGN PATENT DOCUMENTS

| | | |
|---|---|---|
| CN | 103226817 A | 7/2013 |
| CN | 204379742 U | 6/2015 |
| CN | 204562101 U | 8/2015 |
| CN | 105534694 A | 5/2016 |
| CN | 106344127 A | 1/2017 |
| CN | 106821497 A | 6/2017 |
| CN | 106821717 A | 6/2017 |
| CN | 108056910 A | 5/2018 |
| CN | 108143611 A | 6/2018 |
| CN | 108158804 A | 6/2018 |
| KR | 101780319 B1 | 9/2017 |
| WO | 2014204675 A1 | 12/2014 |

\* cited by examiner

METHOD AND DEVICE FOR LOCATING A HUMAN TARGET USING SUPERFICIAL VENOUS CHARACTERISTICS

CROSS-REFERENCES TO RELATED APPLICATIONS

This application is a national stage application filed under 35 U.S.C. 371 based on International Patent Application No. PCT/CN2018/121226, filed on Dec. 14, 2018, which claims priority to Chinese patent application No. 201711414612.5, filed on Dec. 15, 2017, and Chinese patent application No. 201711346243.0, filed on Dec. 15, 2017, disclosures of which are incorporated herein by reference in their entireties.

TECHNICAL FIELD

The present application relates to a method and device for locating a human target using superficial venous characteristics.

BACKGROUND

Medical operations often require the positioning of human targets. The vast majority of human targets are anatomical targets with well-defined anatomical structures that can be clearly defined in image examinations. However, acupoints of Chinese medicine do not have a clear anatomical structure, and they need to be positioned on the body surface according to special methods. The positioning of anatomical targets and the location of acupoints are of great significance in clinical medical operations.

The most common acupoint location is acupuncture at the acupuncture point of Chinese medicine. The proportional bone measurement is the most commonly used, and for patients with different body types, the finger of a doctor is used as the standard of the proportional bone measurement, resulting in a greatly reduced accuracy of positioning. Improper locating will cause unnecessary damage. The most common anatomical target is the puncture and surgery of tissue. The doctor needs to know what anatomical structures are around the punctured tissue or surgically incised tissue. However, on the operating table, only the experience and fuzzy memory at the moment reading the CT can be used, moreover, recall and considering are needed. When anatomical abnormalities are encountered, complications are easily caused.

Clinical biopsy, minimally invasive surgery, internal drainage and many other medical treatments require human puncture operations, including: lumbar puncture, abdominal puncture, lung puncture, kidney puncture, liver puncture, etc., but how to accurately puncture to the goal has always been a problem.

Hemoglobin in human blood has strong ability to absorb infrared light, and the surrounding tissue has weak ability to absorb infrared light. So if the interference of visible light is excluded, in infrared imaging, optical contrast is generated in the venous blood vessel and surrounding tissue, so that the position of the subcutaneous venous blood vessels is clearly displayed. The exact infrared band can be further obtained by analyzing the spectrum of human blood. Therefore, using this specific-band near infrared to make a human surface blood vessel display instrument, the user can use the display device to scan and image the blood vessels under their surface skin, thereby accurately locating the blood vessel.

The morphology of the surficial veins does not change fundamentally with age, and the position on the body surface is relatively fixed. Therefore, the positional relationship between the tissues in the body and the surficial veins is also fixed, and the surficial veins are suitable as an anchor point for locating.

SUMMARY

The application provides a method and device for locating a human target using superficial venous characteristics, which can realize accurate location of the human target, and the device used has a simple structure and a low cost.

To solve the above technical problems, the present application adopts the following solutions.

A method for locating a human target using superficial vein characteristics, includes: (1) acquiring a model displaying both of the human target and superficial veins; (2) projecting the model in the step (1) on a body surface where the superficial veins are located, so that a ratio of a projection on the body surface to actual dimensions of a human body is (0.9-1.1):1; or printing, by using a transparent material, the model in the step (1) according to a size ratio, (0.9-1.1):1, of the model to a human body so as to form a superficial vein mold; and (3) adjusting a position of the projection of the model in the step (2), observing the superficial veins, and making at least two of the superficial veins coincide with veins in the projection of the model, and determining that a position of the human target in the projection of the model is a projection of the human target on the actual body surface; or placing the superficial vein mold in the step (2) on a body surface of a user, adjusting a position of the superficial vein mold, observing the superficial veins, and making at least two of the superficial veins coincide with veins in the superficial vein mold, and determining that a position of the human target on the superficial vein mold is a projection of the human target on the actual body surface.

Using the above method, the human body target of the patient is determined accurately in the first step, and then a model displaying both of the human target and superficial veins is acquired, it can be ensured that the position of the human target is highly consistent with that of step (1). In step (1), the model displaying both of the human target and the veins is based on the body surface where the human body target is located or the vertical projection of the human target and the veins is located. The established model improves the accuracy of human target re-location.

Optionally, in the step (2), the model in step (1) is projected on the body surface where the superficial veins are located such that the ratio of the projection on the body surface to the actual dimensions of the human body is (0.95-1.05):(0.95-1.05); or, the model in the step (1) is printed according to the size ratio (0.95-1.05):(0.95-1.05) by using the transparent material to obtain the superficial vein mold.

Optionally, in the step (2), the model in the above step (2) is printed in a size ratio of 1:1 to the human body by using a transparent material, and the printed model is placed on the body surface where the human target needs to be located; or the model of step (1) is projected on the body surface where the human target is located, the size ratio of the body surface projection to the actual human target is 1:1.

The above (0.95-1.05):(0.95-1.05) or 1:1 size ratio means that the size ratio of the veins, printed in or projected into the surficial vein model, to the veins of the corresponding body of the human body is (0.95-1.05):(0.95)-1.05) or 1:1. That is, the veins in the model are placed or projected onto the corresponding body in an equal proportion, and the veins in the model are coincident with the veins of the body, and the position of the human target in the model is the corresponding target position of the human target.

When the acupoint is located, the model displaying both of the human target and superficial veins is obtained by the vein display device in step (1); the step (1) is completed under a standard condition, which is directly above the body surface with a distance of 10-40 cm and an illuminance of 300-1000 lumens. Optionally, the distance to the body surface is 20-25 cm and the illuminance is 500-800 lumens. The step (3) includes: displaying superficial veins by a vein display device, then adjusting a position of the model printed or projected in step (2) or adjusting the body to make at least two of the superficial veins coincide with veins in the projection of the model, and determining that a position of the human target on the model or in the model projected is a projection of the human target on the actual body surface.

When the acupoint is located, as a solution of the present application, the step (1) includes: finding the acupoint and marking a shootable sign on the body surface, and acquiring, by a vein display device, a picture displaying both of the acupoint and the superficial veins as the model.

When the acupoint is located, as another solution of the present application, the step (1) includes: accurately finding the acupoint and marking a shootable sign on the body surface, scanning a body surface of a patient by a three-dimensional (3D) scanner to establish a 3D model, and acquiring a picture jointly displaying both of the acupoint and the superficial veins by a vein display device, and the picture is incorporated merging the picture to obtain a dermal 3D model including the acupoint and the superficial veins.

When the acupoint is located, as another solution of the present application, the step (1) includes: accurately finding the acupoint and marking a shootable sign on the body surface, scanning the body surface of a patient by a 3D scanner to establish a 3D model, acquiring a picture displaying both of the acupoint and the superficial veins by a vein display device, merging the picture into the 3D model to obtain a dermal 3D model including the acupoint and the superficial veins, and unfolding the dermal 3D model to form a two-dimensional model.

When the acupoint is located, as another solution of the present application, the step (1) includes: acquiring, by a vein display device, a picture of the superficial veins of a patient according to a posture of a standard acupoint map, where the picture includes at least two edges or at least two bone standard points of a body of the patient; expanding or shrinking a body of a target acupoint on the standard acupoint map to a same size as the body in the picture of the superficial veins; and performing a registration on the edges or the bone standard points of the body in the expanded or shrunk standard acupoint map with corresponding edges or corresponding bone standard points of the body in the picture of the superficial veins, and then merging and superimposing into one picture to obtain the model displaying both of the acupoint and the superficial veins.

When the acupoint is located, as another solution of the present application, the step (1) includes: accurately finding the acupoint and marking a shootable sign on the body surface, and acquiring a picture displaying both of the acupoint and the superficial veins by a vein display device; in a case where the acupoint needs to be located again, acquiring, by the vein display device, a vein map of a target acupoint at a same angle through making a patient take a same posture at the time the picture is acquired; and performing a registration on the picture displaying both of the acupoint and the superficial veins and the vein map of the target acupoint to obtain the model displaying both of the acupoint and the superficial veins.

Step 1) of the above various schemes, in order to make the position of the veins and acupoints be displayed more obviously, the established models can be processed to deepen the display of veins and acupoints, and the model may be subjected to image enhancement algorithm processing. The image enhancement algorithm processing may be binarization processing or the like.

When an anatomical target is located, the step (1) of acquiring the model displaying both of the anatomical target and the superficial veins specifically includes: scanning, by a computed tomography (CT) device or a magnetic resonance imaging (MRI) device, the anatomical target and the superficial veins within 1 cm under a superficial layer, parallel to a scanning layer, of the human body, and establishing the model displaying both of the anatomical target and the superficial veins by an image processing software. The step (3) includes displaying the veins of the surface where human target is located by a vein display device, then adjusting a position of the model printed or projected in step (2), or adjusting the body, to make at least two of the superficial veins to coincide with veins in the projection of the model, and determining that a position of the human target on the model printed or projected is a projection, on the actual body surface, of the human target.

When an anatomical target is located, the method of establishing the model displaying both of the anatomical target and the superficial veins includes: (A1) acquiring a tomographic image including the superficial veins and the anatomical target of the human body; (A2) processing, by the image processing software, the tomographic image including the superficial veins in the step (A1), and extracting a superficial vein image; and (A3) normalizing the superficial vein image obtained in step (A2) and a tomographic image of the human target to establish the model with same dimensions and same coordinates.

When an anatomical target is located, as a solution of the present application, normalizing in step (A3) means processing the superficial vein image obtained in step (A2) and the tomographic image of the anatomical target according to uniform dimensions and uniform coordinates. All images of a conventional tomography are in a same coordinate system.

When the anatomical target is located, as another solution of the present application, in step A3), a scale is added to the model. The scale is a scale that comes with the tomography device. It is convenient for checking whether the model and the actual ratio are appropriate that the scale is set on the model.

When the anatomical target is located, as another solution of the present application, in the step A2), the superficial vein image is extracted by a matting method.

When the human target is located, the projecting in step (2) includes: (B1) acquiring the model displaying both of the human target and the superficial veins and storing the model into a gallery 1; (B2) in a case where the human target needs to be located again, acquiring a superficial vein map and storing the superficial vein map into a gallery 2; and (B3) adjusting the model in the gallery 1 by a computer data processing component, performing an image registration on the model with the superficial vein map in the gallery 2, projecting, by a projector, the model displaying both of the human target and superficial veins in the gallery 1 subjected to the image registration on the body surface, so that the ratio of the projection on the body surface to the actual dimensions of the human body is (0.9-1.1):1, and a position on the body surface corresponding to the human target on the projected model is the human target to be located.

When the acupoint or the anatomical target is located, the computer data processing component in the step (B3) or the step (C3) is provided with image enhancement algorithm software inside the computer data processing component, where the image enhancement algorithm software is configured to analyze and extract characteristics of points, lines or faces in the gallery 1 and the gallery 2, perform a graphic transformation and a coordinate transformation on the model in the gallery 1, and perform the registration on the model in the gallery 1 and the superficial vein map in the gallery 2. Optionally, the graphic transformation includes one of: a rigid transformation, an affine transformation, a projection transformation, or a bending transformation.

The advantage of the above method is that it is not necessary to adjust the body, and the acupoint standard is added to the captured image and then the captured image is projected onto the body surface. Even if the acupoint locating is required again, the position of the body is different from the original position, and the angle and size of the model in the gallery 1 can be adjusted by the computer data processing component and then the model is projected, and the body adjustment step is completed in the computer data processing component.

When the acupoint or the anatomical target is located, the superficial vein mold used in the step (2) includes the transparent material on which a superficial vein map is provided. Optionally, a target hole or a puncture channel is also provided. For convenience of use, a model frame is embedded on a periphery of the transparent material, where the model frame is a tubular frame or a semi-tubular frame. The model frame can be selected according to the position where it is located.

The body surface locating model described above is also the model printed in step (2) of the foregoing method. The vein map in the locating model is identical in size and shape to the vein image of the body where the portion to be positioned is located.

The vein display device includes an infrared light source, a computer data processing component, a control component and a liquid crystal display which are connected in sequence. Optionally, the vein display device includes an infrared light source, an infrared filter, an electronic camera, a computer data processing component, a control component and a liquid crystal display which are connected in sequence. When a projector is installed, the projector is connected to the computer data processing component; a spectroscope is disposed in front of the projector, a light outgoing path of the projector is perpendicular to a light incoming path of the electronic camera, the spectroscope is disposed at an intersection of the light outgoing path of the projector and the light incoming path of the electronic camera and is at an angle of 45° with each of the light outgoing path and the light incoming path; and the spectroscope is a band pass filter and is configured to selectively transmit visible light and reflect near-infrared light. Infrared filter protects the imaging system from visible light, making most of the visible light filtered out. The infrared filter may be placed at the bottom of the electronic camera.

A device for locating a human target using superficial vein characteristics, includes: a vein display device, a brace and a human target matching device, where the brace includes a ring-shaped bracket and a plurality of legs connected to the ring-shaped bracket; the vein display device is disposed on the ring-shaped bracket; and the human target matching device is a superficial vein mold or a projector, where the superficial vein mold includes a transparent material on which a vein map and a human target hole are disposed; and in a case where the human target matching device is the projector, the projector is connected to the vein display device.

During use, when the superficial vein mold is included, the superficial vein mold is placed on the body surface where the human body target need to be located, and when at least two veins in the vein body displayed by the vein display device coincide with the veins in the superficial vein mold, the superficial position corresponding to the human target on the mold is the projection of the human target, a sign is marked on the body surface with a pen through the target hole on the superficial vein mold.

The ring-shaped bracket is provided with a support ring for supporting the vein display device, the support ring may clamp the vein display device in pairs, or may be fitted with the vein display device through a gear, and the vein display device can be moved up or down on the ring frame to adjust the distance between the vein display device and the body surface.

At least three legs are provided, and each leg includes a slip ring and a support rod connected to the slip ring, where the slip ring is sleeved on the ring-shaped bracket. Optionally, there are three brackets, which not only saves cost and space, but also ensures the stability of the device.

Optionally, the slip ring is horizontally slidable relative to the ring-shaped bracket and cannot be rotated up and down. As a solution, the cross-section of a tube of the ring-shaped bracket is non-circular, and the hole of the slip ring is also non-circular, so that the slip ring may be prevented from rotating around the ring-shaped bracket; or a locking knob that limits the rotation of the sliding ring on the ring-shaped bracket is provided on the slip ring. Thus, the cross-section of the ring-shaped bracket may be a perfect circle, and the hole of the slip ring may also have a perfect circular shape, and the locking knob can limit the rotation of the slip ring on the ring-shaped bracket.

In order to improve the flexibility of use of the device, the support rod includes a first support rod and a second support rod which are rotatably connected, where the first support rod is connected to the slip ring; the slip ring and the first support rod may be fixedly connected or may be movable connection.

As another solution of the present application, the support rod is arc-shaped, an end of the support rod is connected to the slip ring, and the other end of at least one support rod is provided with an arc-shaped snap ring, where a bottom of the arc-shaped snap ring is a soft structure. In this way, the snap ring can be stuck on the arm and the like without causing discomfort, which not only ensures the comfort of the human body, but also ensures the stability of the use of the device.

As a solution of the present application, the first support rod is rotatably connected to the second support rod through the folding joint, and the first support rod and the second support rod can be folded, or can be opened at an angle and locked at an angle, the movable angle is 0-180 degrees; the device for locating a human target using superficial vein characteristics further includes a base, and the support rod is inserted into the base. The first support rod can also be inserted into the base after merging and can be adjusted to meet the needs of different heights or different positions by adjusting the angle of the first support rod and the angle of the second support rod.

The slip ring is sleeved on the ring-shaped bracket and can slide relative to the ring-shaped bracket. All the first support rods can be merged in a row, which is convenient for holding by hand or packaging, and can also be opened around, forming a tripod to be stably supported above the body surface.

In the present application, the terms, such as bottom, top, top and bottom, refer to the relative positions of the device for normal use.

The computer data processing component is used to process the image acquired by the electronic camera, and is processed by the built-in algorithm and image enhancement algorithm to send the image to the liquid crystal display. The specific method is existing art. The control component is used to control the operation of the vein display device, and the operation of the vein display device can be controlled by a button or by a remote controller, and the existing art may be referred to for the details.

Techniques not mentioned in the present application refer to the existing art.

Figure 1:
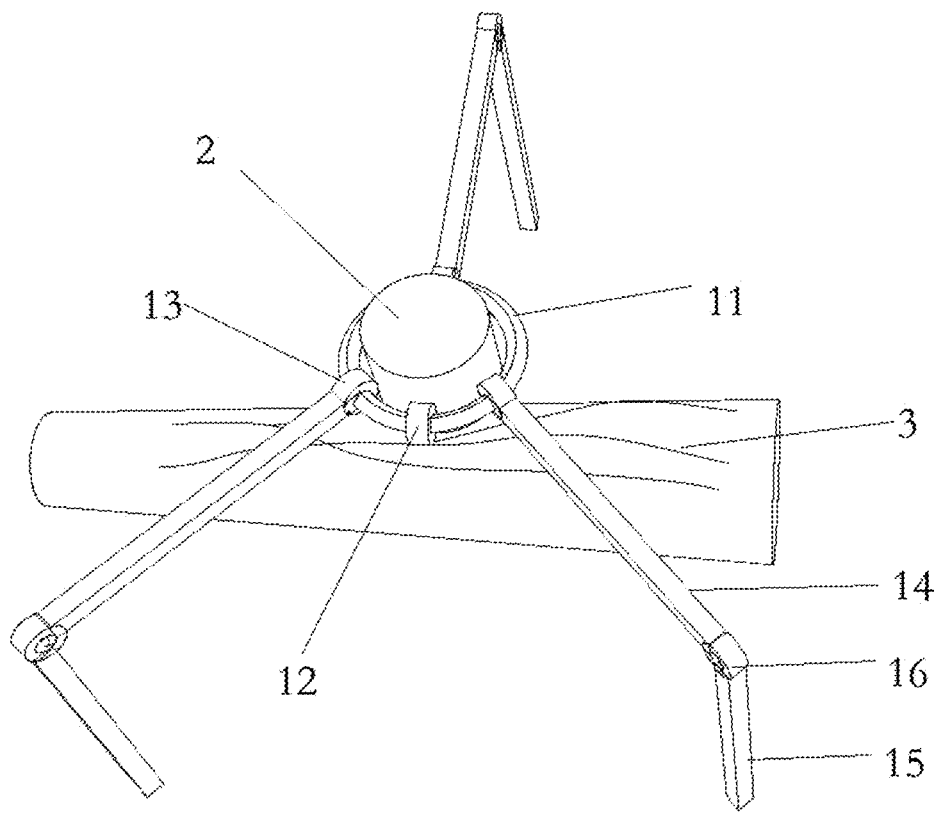
FIG. 1 is a schematic diagram of a device for locating a human target using superficial vein characteristics according to Embodiment 1.

In the drawings: 1: brace; 2: vein display device; 3: an acupoint locating model; 4: superficial vein; 11: ring-shaped bracket; 12: support ring; 13: slip ring; 14: first support rod; 15: second support rod; 16: folding joint; 17: locking knob; 18: arc-shaped snap ring; 19: base; 20: infrared filter; 21: electronic camera; 22: infrared light source; 23: computer data processing component; 24: control component; 25: liquid crystal display; 26: projector; 32: target; 33: scale; 34: a projector bracket.

DETAILED DESCRIPTION

For a better understanding of the present application, the content of the present application will be further described below in conjunction with embodiments, but is not only limited to the embodiments set forth below.

Embodiment 1

Figure 2:
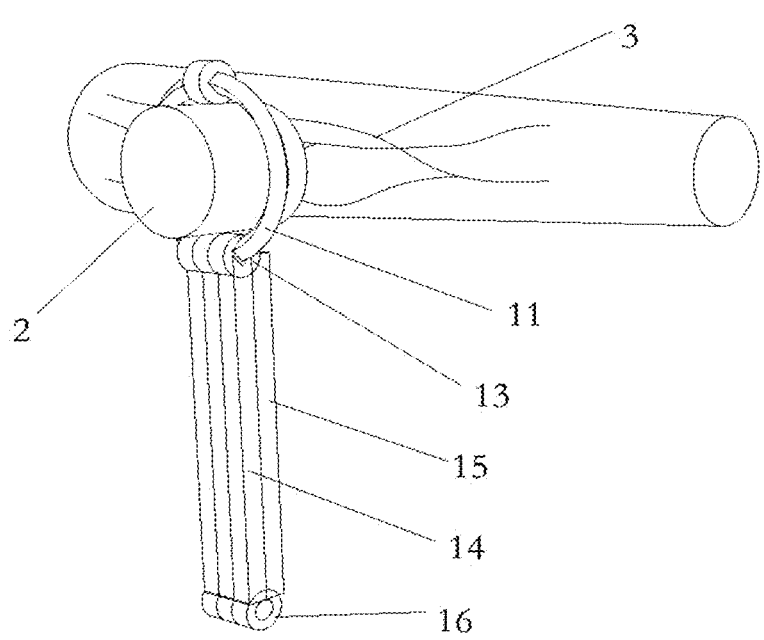
FIG. 2 is a schematic diagram of a device in a folded state for locating a human target using superficial vein characteristics according to Embodiment 1.

As shown in FIG. 1 and FIG. 2, a device for locating a human target using superficial vein characteristics includes a vein display device, a brace and a human target locating model, where the brace includes a ring-shaped bracket and legs connected to each other in up-down direction, and the vein display device is disposed on the ring-shaped bracket. A superficial vein model includes a transparent material on which a vein map and a target hole are arranged.

The vein display device includes an infrared light source, an infrared filter, an electronic camera, a computer data processing component, a control component and a liquid crystal display which are connected to each other in sequence. During use, the liquid crystal display is disposed at a higher position and configured to display a vein of a body, and the infrared light source is disposed at a lower position and configured to irradiate the body.

The ring-shaped bracket is provided with a support ring for supporting the vein display device, where the support ring is fitted with the vein display device through a gear. Three legs are provided, and each of the three legs includes a slip ring and a support rod connected to the slip ring, where the slip ring is sleeved on the ring-shaped bracket.

A cross-section of a tube of the ring-shaped bracket is non-circular, and a hole of the slip ring is also non-circular, so that the slip ring may be prevented from rotating around the ring-shaped bracket.

The support rod includes a first support rod and a second support rod rotatably connected to each other, where the first support rod is connected to the slip ring and is rotatably connected to the second support rod through a folding joint.

During use, the vein display device is placed at an appropriate position through the brace, has a distance of 20 to 30 cm to a body surface, and has an illuminance of 500 to 800 lumens. Thus, it is convenient for the vein display device to display the vein of the body at the position of the human target to be determined. A user or another person observes the liquid crystal display of the vein display device from which superficial veins of the user and the vein map of the human target locating model can be simultaneously observed. A position of a body of the user and a position of a superficial vein model are adjusted to make at least two of the superficial veins of the user coincide with at least two veins in the vein map of the human target locating model. At this time, a superficial position corresponding to a target point on the human target locating model is a position or a projection, on the body surface, of the human target to be located.

Embodiment 2

The embodiment 2 is basically the same as the embodiment 1, and a difference lies in that the human target locating model is not included, and a projector is included. The projector is connected to the computer data processing component, and a spectroscope is disposed in front of the projector. A light outgoing path of the projector is perpendicular to a light incoming path of the electronic camera. The spectroscope is disposed at an intersection of the light outgoing path and the light incoming path and is at an angle of 45° with each of the light outgoing path and the light incoming path. The spectroscope is a band pass filter, and is configured to selectively transmit visible light and reflect near-infrared light.

The projector vertically projects an image including the vein map and an acupoint position to the body surface, and the user or another person observes the liquid crystal display of the vein display device from which the superficial veins of the user and the projected vein map can be simultaneously observed. A position of the body of the user and a position of the projector are adjusted to make at least two of the superficial veins of the user coincide with at least two veins in the projected vein map. At this time, the superficial position corresponding to the target point on the projected image is the position or the projection, on the body surface, of the human target to be located.

Embodiment 3

The embodiment 3 is basically the same as the embodiment 1, and a difference lies in that the slip ring is provided with a locking knob for preventing the slip ring from rotating around the ring-shaped bracket.

Embodiment 4

Figure 3:
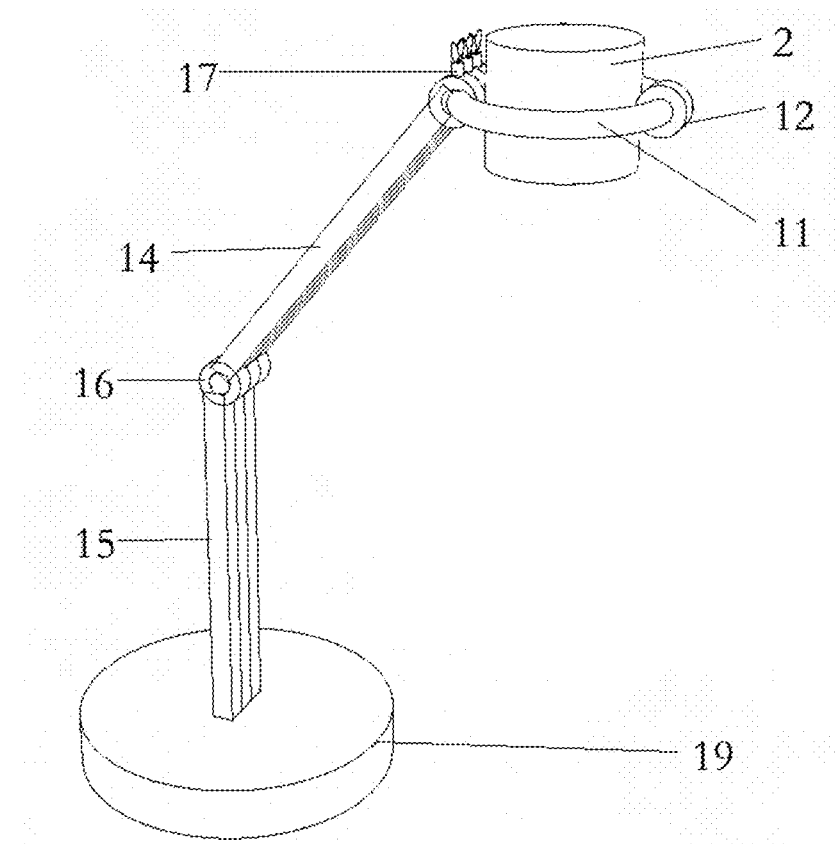
FIG. 3 is a schematic diagram of a device for locating a human target using superficial vein characteristics according to Embodiment 4.

As shown in FIG. 3, the embodiment 4 is basically the same as the embodiment 3, and a difference lies in that: the device for locating a human acupoint using superficial vein characteristics further includes a base, a bottom of the second support rod is inserted into the base.

Embodiment 5

Figure 4:
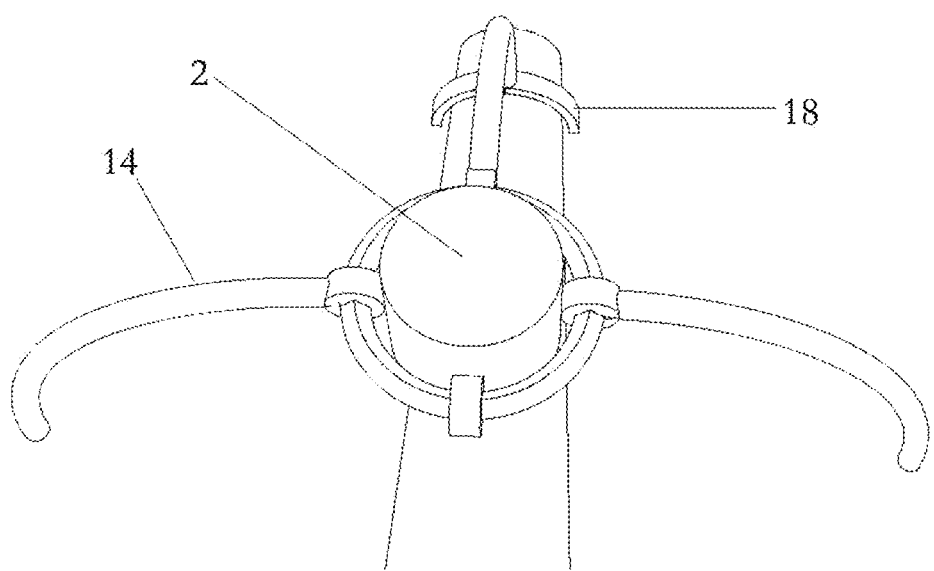
FIG. 4 is a schematic diagram of a device for locating a human target using superficial vein characteristics according to Embodiment 5.
Figure 5:
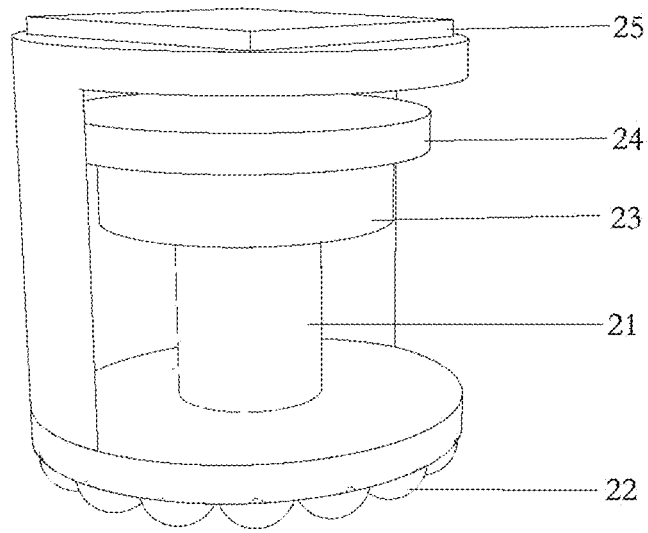
FIG. 5 is a schematic diagram of a device for vein display.

As shown in FIG. 4, the embodiment 5 is basically the same as the embodiment 1, and a difference lies in that: the support rod is arc-shaped, one end of the support rod is connected to the slip ring, and the other end of the support rod is provided with an arc-shaped snap ring, where a bottom of the arc-shaped snap ring is a soft structure.

Embodiment 6

The embodiment 6 is basically the same as the embodiment 1, and a difference lies in that a periphery of the transparent material is embedded with a model frame which is a tubular or semi-tubular frame.

Application Embodiment 1

Figure 6:
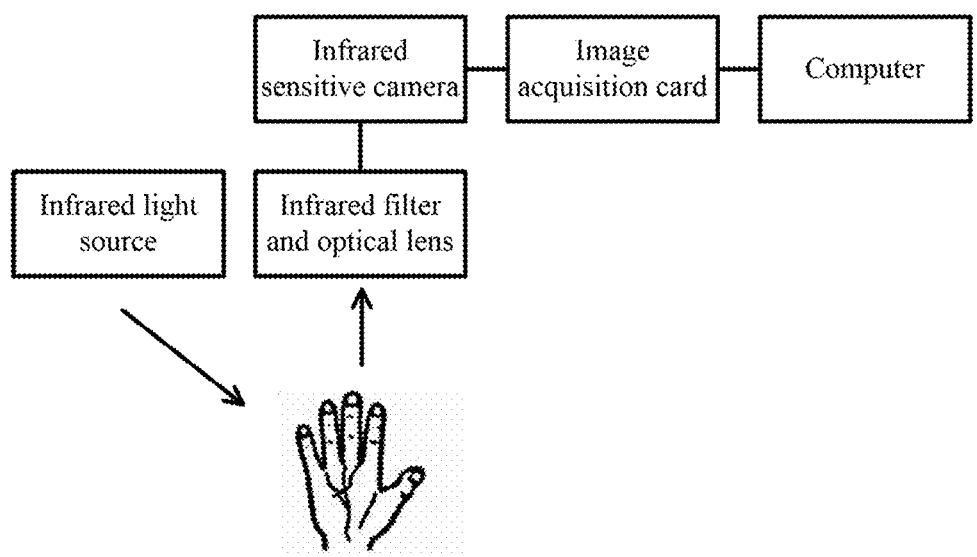
FIG. 6 is a schematic diagram according to Application embodiment 1.

As shown in FIG. 6, in a case where an acupoint is located, a method for locating human target using superficial vein characteristics includes the steps below.

1) The acupoint is accurately found and a shootable sign is marked on the body surface, and a picture, as the model, displaying both of the acupoint and the superficial veins is acquired by a vein display device.

2) The model in step (1) is printed according to the ratio (1:1) by using a transparent material, a hole is punched on the shootable sign of the superficial vein model, and the superficial vein model is placed on the body surface.

3) A vein of the body where acupoint is to be located is displayed with a vein display device; a position of the model printed in step 2 is adjusted, or a position of the body is adjusted, to make at least two of the body coincide with veins in the printed model; and it is determined that a superficial position corresponding to the acupoint on the printed model is the position of the to-be-located acupoint. A sign may be marked on the body surface with a pen through the hole at the position of acupoint of the printed model.

Application Embodiment 2

In a case where an acupoint is located, a method for locating human target using superficial vein characteristics includes the steps below.

1) The acupoint is accurately found and a shootable sign is marked on the body surface, the body surface of a patient is scanned by a 3D scanner to establish a 3D model, a picture displaying both of the acupoint and the superficial veins is acquired by a vein display device, and the picture is merged into the 3D model to obtain a dermal 3D model including the acupoint and the veins.

2) The model in step (1) is printed according to the ratio (1:1), a hole is punched on the shootable sign of the superficial vein model, and the superficial vein model is placed on the body surface.

3) A vein of the body where acupoint is to be located is displayed with a vein display device; a position of the printed 3D model in step (2), model printed in step 2 is adjusted, or a position of the body is adjusted, to make at least two of the superficial veins of the body coincide with veins in the printed model, and it is determined that a superficial position corresponding to the acupoint on the printed model is the position of the to-be-located acupoint. A sign may be marked on the body surface with a pen through the hole at the position of acupoint of the printed model.

Application Embodiment 3

In a case where an acupoint is located, a method for locating human target using superficial vein characteristics includes the steps below.

1) The acupoint is accurately found and a shootable sign is marked on the body surface, the body surface of a patient is scanned by a 3D scanner to establish a 3D model, a picture displaying both of the acupoint and the superficial veins is acquired by a vein display device, the picture is merged into the 3D model to obtain a dermal 3D model including the acupoint and the veins, and the dermal 3D model is unfolded to form a two-dimensional model.

2) The two-dimensional model in step (1) is printed according to the ratio (1:1), a hole is punched on the shootable sign of the superficial vein model, and the superficial vein model is placed on the body surface.

3) A vein of the body where acupoint is to be located is displayed with a vein display device; a position of the printed two-dimensional model in step (2), model printed in step 2 is adjusted, or a position of the body is adjusted, to make at least two of the superficial veins of the body coincide with veins in the printed model, and it is determined that a superficial position corresponding to the acupoint on the printed model is the position of the to-be-located acupoint. A sign may be marked on the body surface with a pen through the hole at the position of acupoint of the printed model.

Application Embodiment 4

Figure 7:
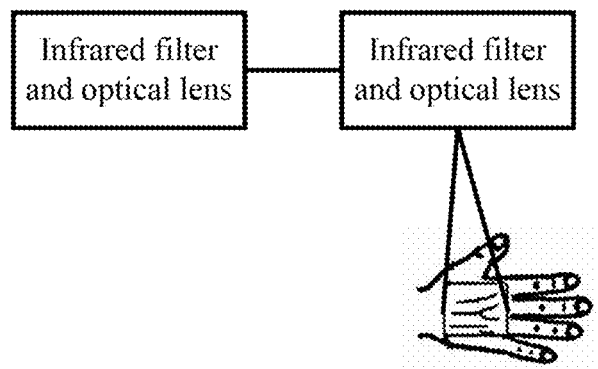
FIG. 7 is a schematic diagram according to Application embodiment 4.
Figure 8:
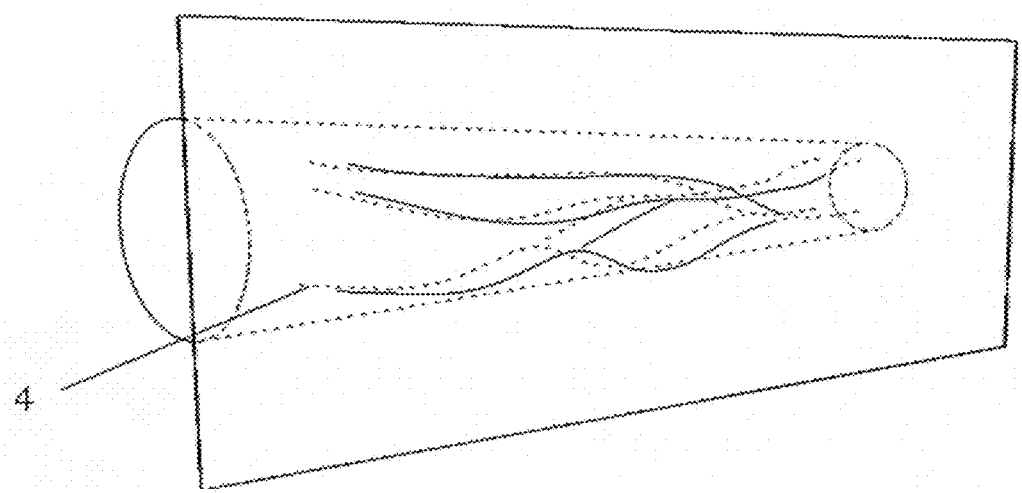
FIG. 8 is a structural schematic diagram of a two-dimensional acupoint locating model (the acupoint hole is omitted)
Figure 9:
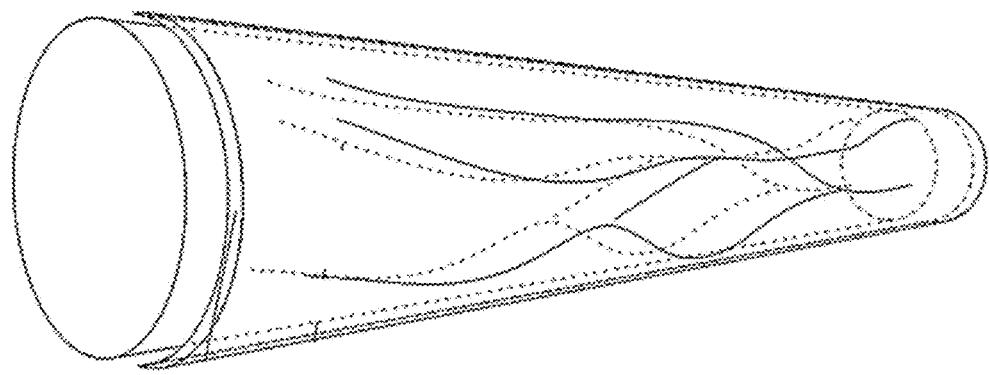
FIG. 9 is a structural schematic diagram of the 3D acupoint locating model (the acupoint hole is omitted)
Figure 10:
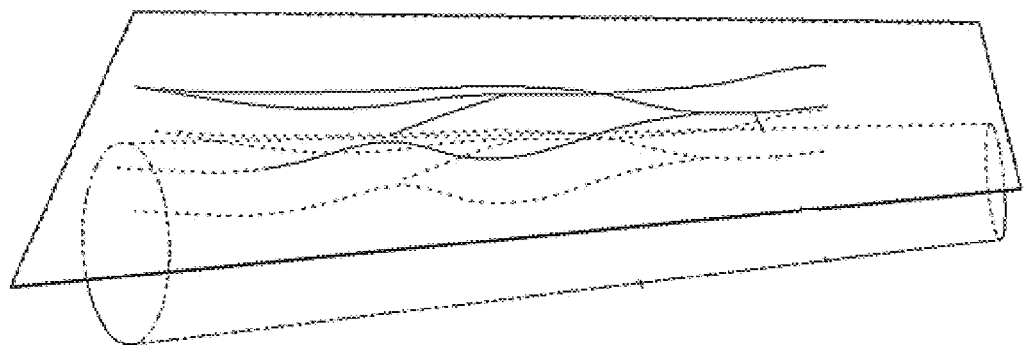
FIG. 10 is a structural schematic diagram of FIG. 9 after flattening.

As shown in FIG. 7, in a case where an acupoint is located, a method for locating human target using superficial vein characteristics includes the steps below.

1) The acupoint is accurately found and a shootable sign is marked on the body surface, and a picture, as the model, displaying both of the acupoint and the superficial veins is acquired by a vein display device.

2) The model in step (1) is projected on a body surface where the acupoint is located according to the ratio (1:1) to a human body.

3) A vein of the body where acupoint is to be located is displayed with a vein display device; a position of the projection of the model in step 2 is adjusted, or a position of the body is adjusted, to make at least two of the body coincide with veins in the projected model; and it is determined that a superficial position corresponding to the acupoint on the printed model is the position of the to-be-located acupoint. A sign may be marked on the body surface with a pen.

Application Embodiment 5

In a case where an acupoint is located, a method for locating human target using superficial vein characteristics includes the steps below.

1) The acupoint is accurately found and a shootable sign is marked on the body surface, and a picture displaying both of the acupoint and the superficial veins is acquired by a vein display device; in a case where the acupoint needs to be located again, a vein map of a target acupoint is acquired, by the vein display device at a same angle, through making a patient take a same posture at the time the picture is acquired; the vein map and the picture displaying both of the acupoint and the superficial veins are processed respectively by image enhancement algorithm; and then a registration is performed on the vein map and the picture displaying both of the acupoint and the superficial veins to obtain the model displaying both of the acupoint and the superficial veins.

2) The model in step (1) is projected on a body surface where the acupoint is located according to the ratio (1:1) to a human body.

3) A vein of the body where acupoint is to be located is displayed with a vein display device; the registration is performed on the vein map and the model acquired in step (1), finally making the projection of veins in the model on the body surface is completely coincided with the main veins under skin; and it is determined that a superficial position corresponding to the acupoint on the printed model is the position of the to-be-located acupoint. A sign may be marked on the body surface with a pen.

Application Embodiment 6

In a case where an acupoint is located, a method for locating human target includes the following steps.

1) A picture of the superficial veins of a patient is acquired by a vein display device according to a posture of a standard acupoint map, where the picture includes at least two edges or at least two bone standard points of a body of the patient; a body of a target acupoint on the standard acupoint map is expanded or shrunk to a same size as the body in the picture of the superficial veins; and a registration is performed on the edges or the bone standard points of the body in the expanded or shrunk standard acupoint map with corresponding edges or corresponding bone standard points of the body in the picture of the superficial veins, merging and superimposing into one picture, and then image enhancement algorithm processing is performed on the picture, so that the model displaying both of the acupoint and the superficial veins is obtained.

2) The model in step (1) is printed according to the ratio (1:1) by using a transparent material, a hole is punched on the shootable sign of the superficial vein model, and the superficial vein model is placed on the body surface.

3) A vein of the body where acupoint is to be located is displayed with a vein display device; a position of the model printed in step 2 is adjusted, or a position of the body is adjusted, to make at least two of the body coincide with veins in the printed model; and it is determined that a superficial position corresponding to the acupoint on the printed model is the position of the to-be-located acupoint. A sign may be marked on the body surface with a pen through the hole at the position of acupoint of the printed model.

Application Embodiment 7

In a case where an acupoint is located, a method for locating human target using superficial vein characteristics includes the following steps.

1) The acupoint is accurately found and a shootable sign is marked on the body surface, the body surface is photographed with a vein display device under a standard condition, a standard map is obtained as reference images, the reference model displaying both of the human target and superficial veins is made, and the reference model is stored in reference model gallery. The standard condition is that the model is acquired directly above the body surface with a distance of 20 to 25 cm from the body surface and an illuminance of 500 to 800 lumens.

2) In practical use, when the acupoint needs to be re-located, the body surface is taken with a vein display device to obtain real-time images. by using a computer with X86 framework computer system of the INTEL corporation and with the image enhancement algorithm software installed inside, and running Windows 8 operating system, the point feature, line feature or surface feature of real-time image is analyzed and extracted, and the point feature, line feature or surface feature reference model is analyzed and extracted, and the register is performed on them. A rigid transformation, an affine transformation, projection transformation, or a bending transformation is performed on the reference model, and coordinate transformation is performed on the reference model, so as to make the reference model coincide with the real-time images, and then the transformed reference model is projected onto the body surface. The superficial position corresponding to the acupoint on the projected model is the position of the to-be-located acupoint.

3) In actual use, the real-time image is refreshed 24 times per second, with running step 2 for each time, in this manner the acupoint location can be dynamically displayed.

According to this application embodiment, there is no need to adjust the body, and the reference model obtained under the standard condition is registered according to the actual angle and actual distance, and then the deformed reference model is projected onto the body surface by the shooting angle. Accurate positioning can be achieved even if the position of the body is different from the original position. High-frequency refreshing of the actual captured image enables real-time dynamic display. It is convenient for the user to use.

Application Embodiment 8

In a case where an anatomical target is located, a method for locating human target using superficial vein characteristics includes steps described below.

In step 1, the anatomical target and the superficial veins within 1 cm under a superficial layer, parallel to a scanning layer, of the human body are scanned by a computed tomography (CT) device or a magnetic resonance imaging (MRI) device.

In step 2, a tomographic image including the superficial veins in step 1 is processed by an image processing software, and a superficial vein image is extracted by a matting method.

In step 3, both the superficial vein image and the tomographic image of the anatomical target in step 2 are processed according to uniform dimensions and uniform coordinates and a scale is added to form a model which displays both of a human target and the superficial veins.

In step 4, the model in step 3 is projected on a body surface where the superficial veins are located to make a ratio of a projection on the body surface to actual dimensions of the human body (0.9-1.1):1; or the model in step 1 is printed by using a transparent material according to the ratio (0.9-1.1):1 to obtain a superficial vein mold.

In step 5, a position of the projection of the model in step 4 is adjusted, the superficial veins are observed, and at least two of the superficial veins are made to coincide with veins in the projection of the model, and a position of the human target in the projection of the model is a projection of the human target on the actual body surface; or the superficial vein mold in step 4 is placed on the body surface of a user and its position is adjusted, and the superficial veins are observed and at least two of the superficial veins are made to coincide with veins in the superficial vein mold, and a position of the human target on the superficial vein mold is the projection of the human target on the actual body surface.

Figure 11:
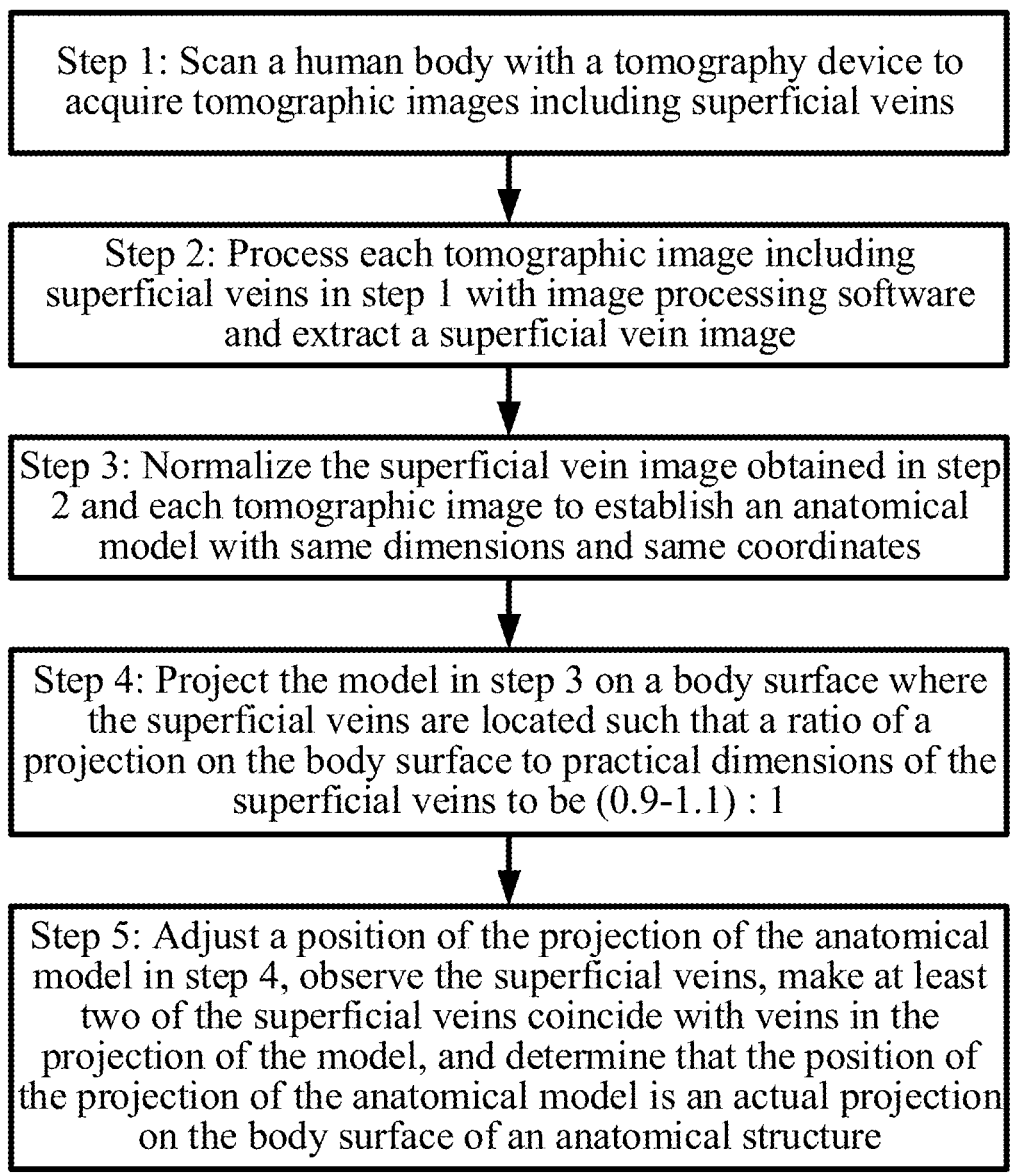
FIG. 11 is a flow chart of a projection method using superficial vein characteristics according to the present application.

In this embodiment, a renal cyst puncture is taken as an example. FIG. 11 is a flowchart of a projection method in the present application.

In step 1, a spatial relationship between a renal cyst and the body surface is learned, the tomographic image including the superficial veins is acquired by scanning the human body with a tomography device.

A conventional continuous tomography device includes CT and MRI, and in this embodiment, the CT is employed to examine the renal cyst. Generally, the CT is concentrated around the target, and coronal and sagittal scanning is generally not performed on the body surface parallel to the scanning layer. At present, the existing superficial vein display device can display veins within 1 cm from the body surface, and veins with larger diameters are easier to be observed. When the human target is captured, an operator is required to specifically scan 1 to 3 layers on the body surface parallel to the scanning layer to scan subcutaneous tissues including the veins under the body surface within 1 cm and then to scan the target according to the same coordinates. If only horizontal scanning is performed, because the superficial veins are traversed, and the horizontal scanning may be reconstructed and simulated to the coronal scanning and sagittal scanning by Mimics medical 17.0 software.

Figure 12A:
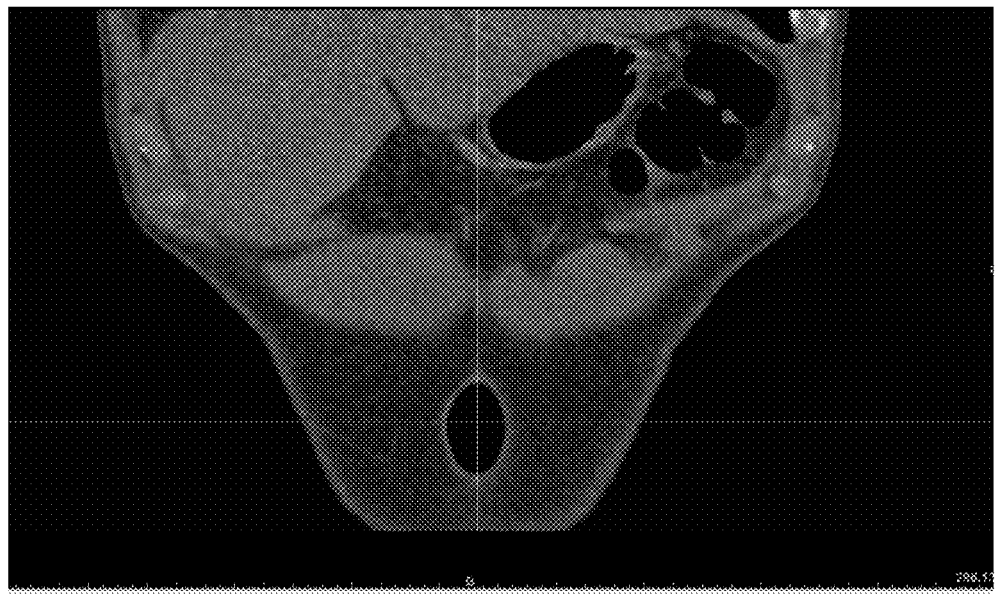
FIG. 12A is a schematic diagram showing a tomographic scan image of surficial veins on a right side of umbilicus in the Application embodiment 8.

In step 2, FIG. 12A is a schematic diagram showing a CT tomographic scan image of surficial veins on a right side of umbilicus in the Application embodiment 8. Referring to FIG. 12A, the hole in the middle of the lower part is a sunken portion of a navel, and the superficial veins which are not apparent can be seen in superficial layers on a right side of the navel. When the CT image is processed using Photoshop, an original image is taken as a background layer, a new image layer is copied on the background layer, a selection including only the superficial veins is depicted by a magnetic lasso function along a edge of the superficial veins on the new image, and the image except the selection is deleted. In this way, FIG. 12B which is a schematic diagram including only the superficial veins which is obtained through processing FIG. 12A in the application embodiment 8.

In other embodiments, color level adjustment, local brightness adjustment, local color adjustment and drawing contour lines on the superficial veins may also be employed to clearly distinguish the superficial veins from other portions of the image.

Figure 12B:
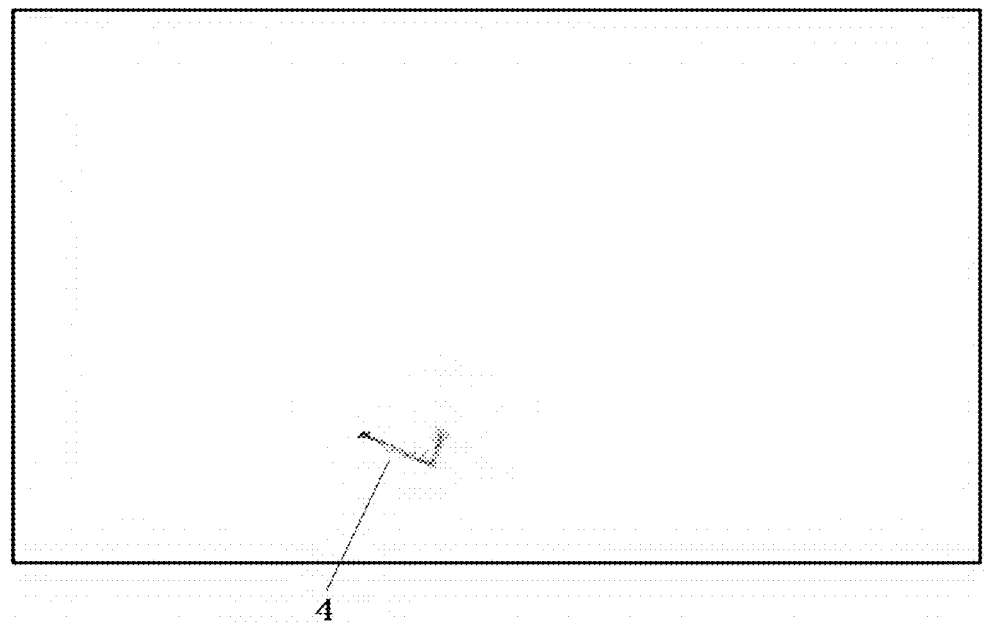
FIG. 12B is a schematic diagram of the image of FIG. 12A after being processed in Application embodiment 8.
Figure 13A:
FIG. 13A is a schematic diagram showing a tomographic scan image of surficial veins on a right side of umbilicus in the Application embodiment 8.
Figure 13B:
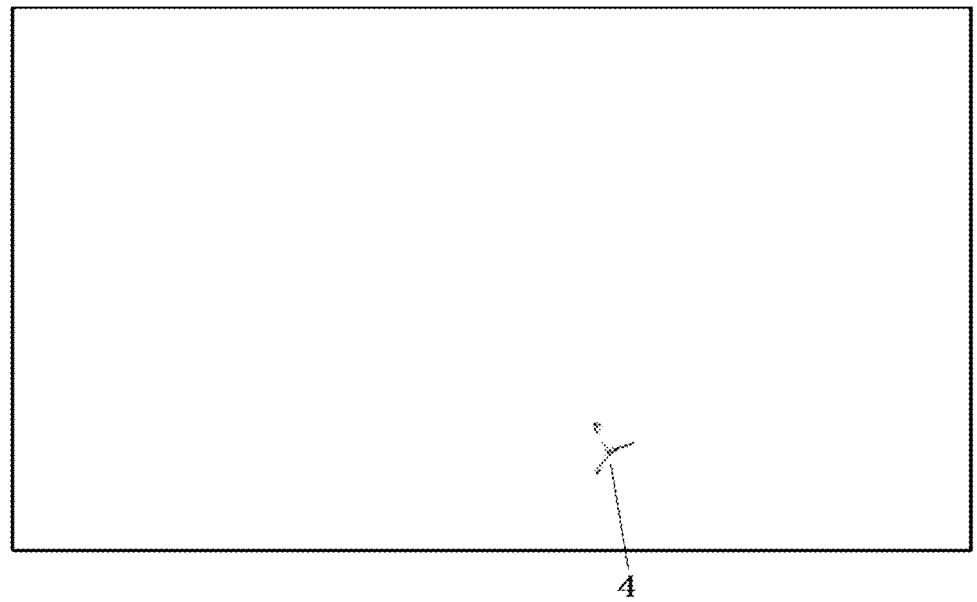
FIG. 13B is a schematic diagram of the image of FIG. 13A after being processed in the Application embodiment 8.
Figure 14A:
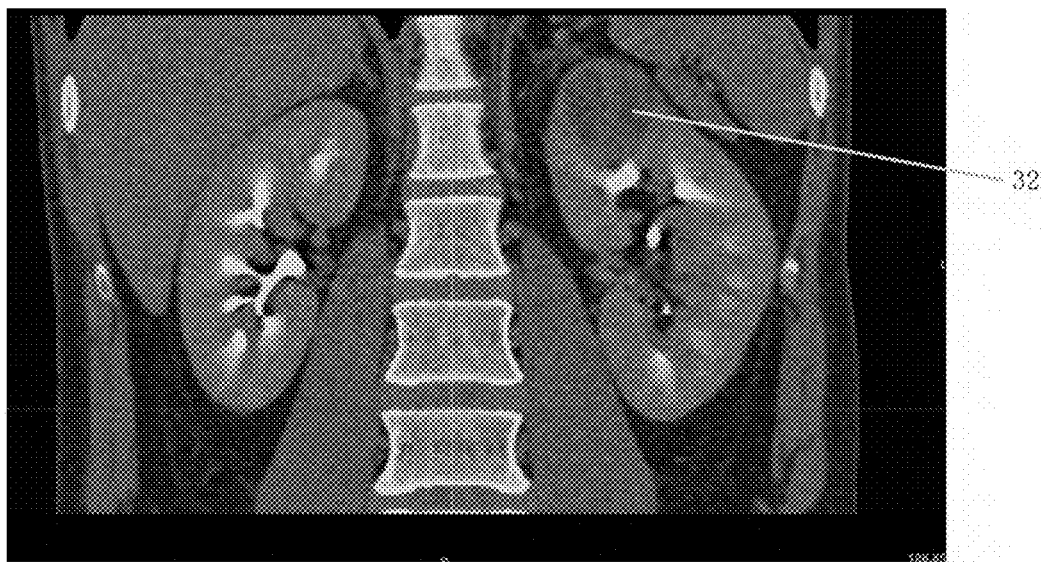
FIG. 14A is a schematic diagram showing a tomographic scan image of a cyst, in an upper part of a left kidney, as a target in Application embodiment 8.
Figure 14B:
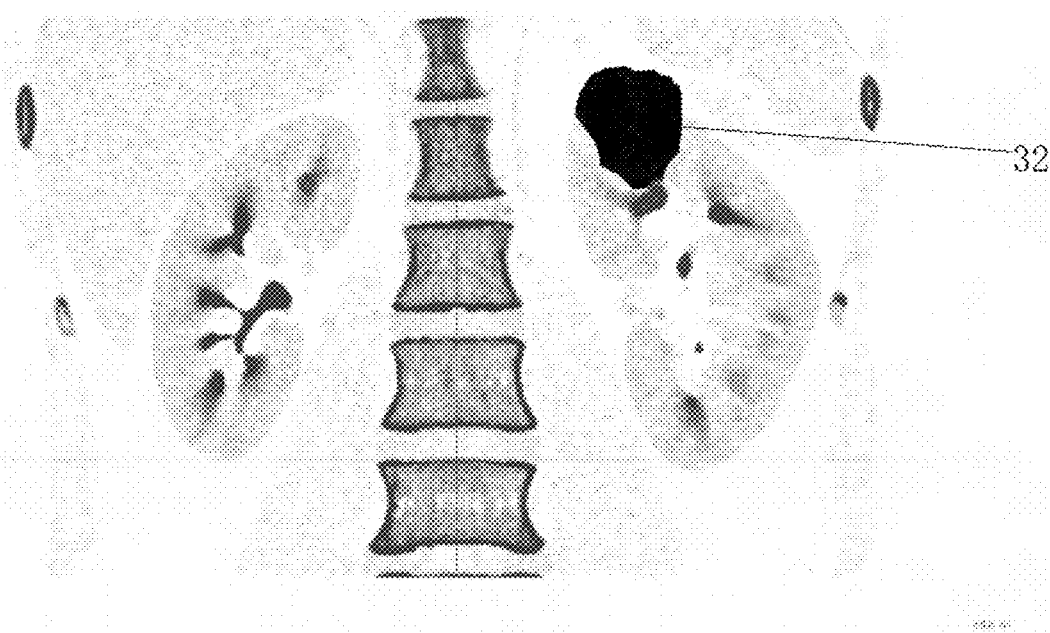
FIG. 14B is a schematic diagram of the processing of FIG. 14A in Application embodiment 8.

FIG. 13A is a schematic diagram of a CT tomographic scan image of superficial veins on a left side of the umbilicus. FIG. 13B is obtained by processing the CT image with the same method described above. FIG. 14A is a schematic diagram of a CT tomographic scan image of a cyst, in an upper part of a left kidney, as the target. A hue inversion function of the Photoshop is employed to inverse black and white to light the background. The CT image is further processed by the method of FIG. 12 to obtain FIG. 14B, where the FIG. 14 is a schematic diagram with the highlighted cyst target and is obtained through processing FIG. 14 in the application embodiment 8.

In step 3, the processed superficial vein image and tomographic scan image of another anatomical target are made into anatomical models with same dimensions and same coordinates.

In the conventional continuous tomography, all images share a common coordinate system and are scaled at the same proportion. Multiple tomographic images obtained in this embodiment are not scaled in dimension and thus still match the original coordinate system. In the conventional continuous tomography, a length scale will be left on the image.

Figure 15:
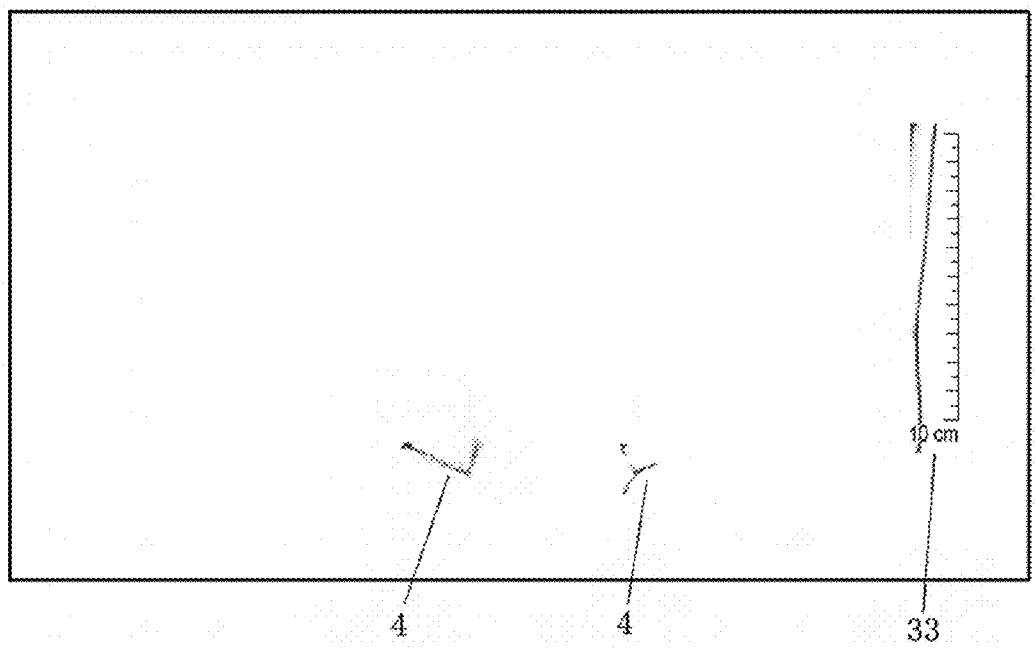
FIG. 15 is a schematic diagram showing a display model displaying both of the superficial vein and the scale in the Application embodiment 8.

FIG. 12B, FIG. 13B and the length scale are pasted on a same blank background image, and all the three images abut against an upper left corner of the background. Even if an alignment sign is not marked in advance, accurate aligning may still be implemented. FIG. 15 which shows a synthesized model of the superficial veins in the application embodiment 8 is obtained. Other tomographic images are also pasted on a blank background image, and all three images abut against an upper left corner of the background to generate a model with the same coordinates and dimensions as the model of the superficial veins.

In a non-limiting application embodiment, the alignment sign is marked with the image processing software in advance at positions with the same coordinates of the images to check whether the images are aligned.

Figure 16:
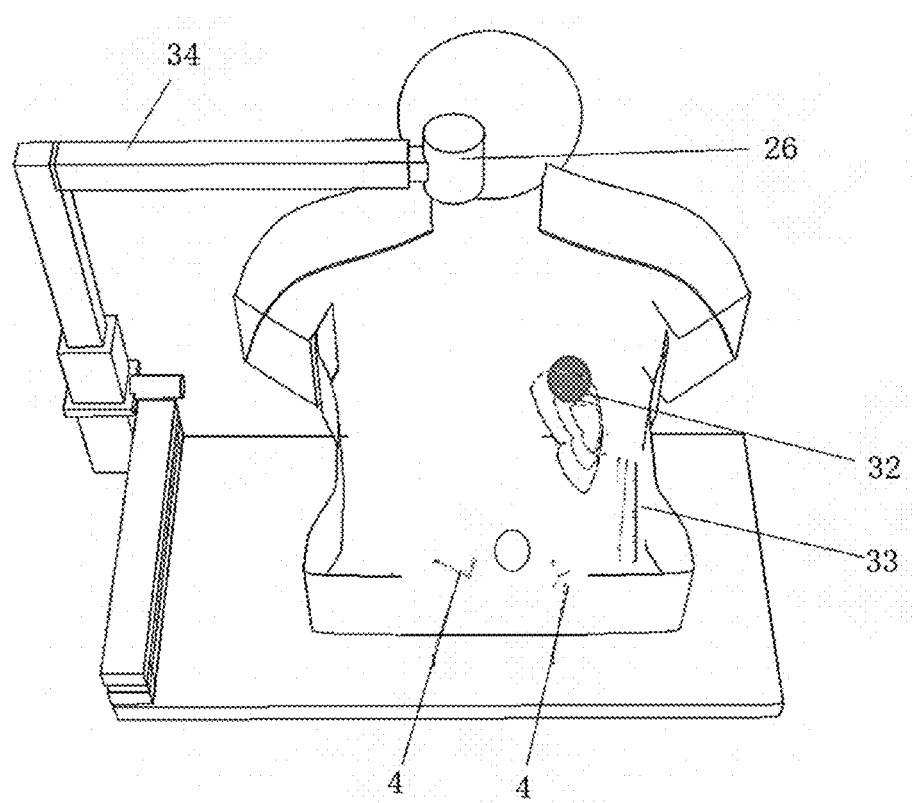
FIG. 16 is a schematic diagram showing projection of an anatomical model on a body surface after locating in Application embodiment 8.

In step 4, as shown in FIG. 16, the models in step 3 are projected on the body surface of the human body, making a ratio of projections on the body surface to the actual dimensions of the human target (0.95-1.05):1. The ratio of the projection on the body surface to the actual dimensions of the human target is calculated by comparing an identification length of the scale with an actual length. The ration is adjusted by adjusting a projection distance or an image size.

In step 5, it may be seen on a vein display that the superficial veins are also projected on the body surface and do not certainly coincide with the actual superficial veins, and a position of the projector or a human body position needs to be adjusted to make the superficial veins in the model coincide with the actual superficial veins. At least two superficial veins in the projection need to coincide with the actual superficial veins, and a position on the body surface corresponding to the target on the projected model is a projection, on the body surface, of a target to be located.

In this application embodiment, a position and an angle at which the model of the superficial veins is projected are adjusted in a computer, so that it may be seen that the actual superficial veins on the body surface are unchanged in a liquid crystal display while the projected model of the superficial is continuously aligned with the actual superficial veins. A vertical distance from the target to the projection on the body surface is denoted by d, where d is equal to the number of layers between the target and the body surface during the CT multiplied by a layer thickness. A size of d may be calculated with the scale after d is directly measured on a CT image.

In a non-limiting application embodiment, a patient is guided to adjust the human body position, so that it may be seen that the projected model of the superficial veins is unchanged in the liquid crystal display and the actual superficial veins of the patient are continuously aligned with the projected model of the superficial veins until at least two superficial veins coincide with the veins in the projected model.

Application Embodiment 9

This application embodiment is similar to the application embodiment 8, except that this application embodiment is used for layer-by-layer locating and projection during a surgery. During the surgery, a vein image projected by the model of the superficial veins coincides with the actual superficial veins and CT or MRI images at different layers and a synthesized three-dimensional (3D) image are projected in a surgery region by a projector fixed on a projector bracket to make the ratio of the projection on the body surface to the actual dimensions of the human body 1:1. During the surgery, different images at different layers may be projected according to the progress of the surgery to remind a surgeon of tissues around the target, improving an accuracy of the surgery and reducing vice-damages.

What is claimed is:

1. A method for locating a human target using superficial vein characteristics, comprising:
   acquiring a model displaying both of the human target and superficial veins;
   projecting the model on a body surface where the superficial veins are located, so that a ratio of a projection on the body surface to actual dimensions of a human body is (0.9-1.1): 1; or printing, by using a transparent material, the model according to a size ratio, (0.9-1.1): 1, of the model to a human body so as to form a superficial vein mold; and
   adjusting a position of the projection of the model, observing the superficial veins, and making at least two of the superficial veins coincide with veins in the projection of the model, and determining that a position of the human target in the projection of the model is a projection of the human target on the actual body surface; or placing the superficial vein mold on the body surface, adjusting a position of the superficial vein mold, observing the superficial veins, and making at least two of the superficial veins coincide with veins in the superficial vein mold, and determining that a position of the human target on the superficial vein mold is a projection of the human target on the actual body surface.

2. The method of claim 1, wherein the human target is an acupoint.

3. The method of claim 1, wherein the human target is an anatomical target.

4. The method of claim 1, wherein observing the superficial veins comprises observing the superficial veins by a vein display device.

5. The method of claim 2, wherein the step of acquiring the model displaying both of the human target and superficial veins is performed under a standard condition, and the standard condition is that a vein display device for acquiring a model displaying both of the human target and superficial veins is disposed directly above the body surface with a distance of 10 to 40 cm from the body surface and an illuminance of 300 to 1000 lumens.

6. The method of claim 2, wherein acquiring the model displaying both of the acupoint and the superficial veins comprises: finding the acupoint and marking a shootable sign on the body surface, and finally acquiring a picture displaying both of the acupoint and the superficial veins as the model.

7. The method of claim 2, wherein the acquiring the model displaying both of the human target and superficial veins comprises: accurately finding the acupoint and marking a shootable sign on the body surface, scanning the body surface by a three-dimensional (3D) scanner to establish a 3D model, acquiring a picture displaying both of the acupoint and the superficial veins by a vein display device, and merging the picture into the 3D model to obtain a dermal 3D model including the acupoint and the superficial veins.

8. The method of claim 2, wherein the acquiring the model displaying both of the human target and superficial veins comprises: accurately finding the acupoint and marking a shootable sign on the body surface, scanning the body surface by a 3D scanner to establish a 3D model, acquiring a picture displaying both of the acupoint and the superficial veins by a vein display device, merging the picture into the 3D model to obtain a dermal 3D model comprising the acupoint and the superficial veins, and unfolding the dermal 3D model to form a two-dimensional model.

9. The method of claim 2, wherein the acquiring the model displaying both of the human target and superficial veins comprises:
   acquiring, by a vein display device, a picture of the superficial veins according to a posture of a standard acupoint map, wherein the picture comprises at least two edges or at least two bone standard points of the human body;
   expanding or shrinking a body of a target acupoint on the standard acupoint map to a same size as the body in the picture of the superficial veins; and
   performing a registration on the edges or the bone standard points of the body in the expanded or shrunk standard acupoint map with corresponding edges or corresponding bone standard points of the body in the picture of the superficial veins, and then merging and superimposing into one picture to obtain the model displaying both of the acupoint and the superficial veins.

10. The method of claim 2, wherein the acquiring the model displaying both of the human target and superficial veins comprises:
   accurately finding the acupoint and marking a shootable sign on the body surface, and acquiring a picture displaying both of the acupoint and the superficial veins by a vein display device;
   in a case where the acupoint needs to be located again, acquiring, by the vein display device, a vein map of a target acupoint at a same angle through making a patient take a same posture at the time the picture is acquired; and
   performing a registration on the picture displaying both of the acupoint and the superficial veins and the vein map of the target acupoint to obtain the model displaying both of the acupoint and the superficial veins.

11. The method of claim 3, wherein the acquiring the model displaying both of the anatomical target and the superficial veins comprises: scanning, by a computed tomography (CT) device or a magnetic resonance imaging (MRI) device, the anatomical target and the superficial veins within 1 cm under a superficial layer, parallel to a scanning layer, of the human body, and establishing the model displaying both of the anatomical target and the superficial veins by an image processing software.

12. The method of claim 11, wherein establishing the model displaying both of the anatomical target and the superficial veins by the image processing software comprises:
   acquiring a tomographic image including the superficial veins and the anatomical target of the human body;
   processing, by the image processing software, the tomographic image including the superficial veins, and extracting a superficial vein image; and
   normalizing the superficial vein image and the tomographic image of the anatomical target to establish a model with same dimensions and same coordinates.

13. The method of claim 2, wherein projecting the model on the body surface where the superficial veins are located comprises:
   acquiring the model displaying both of the acupoint and the superficial veins and storing the model into a gallery 1;
   in a case where the acupoint needs to be located again, acquiring a superficial vein map and storing the superficial vein map into a gallery 2; and
   adjusting the model in the gallery 1 by a computer data processing component, performing an image registration on the model with the superficial vein map in the gallery 2, projecting, by a projector, the model displaying both of the acupoint and superficial veins in the gallery 1 subjected to the image registration on the body surface, so that the ratio of the projection on the body surface to the actual dimensions of the human body is (0.9-1.1): 1, and a position on the body surface corresponding to the acupoint on the projected model is the acupoint to be located.

14. The method of claim 3, wherein projecting the model on the body surface where the superficial veins are located comprises:
   acquiring the model displaying both of the anatomical target and the superficial veins and storing the model into a gallery 1;
   in a case where the anatomical target needs to be located again, acquiring a superficial vein map and storing the superficial vein map into a gallery 2; and
   adjusting the model in the gallery 1 by a computer data processing component, performing an image registration on the model with the superficial vein map in the gallery 2, projecting, by a projector, the model displaying both of the anatomical target and superficial veins in the gallery 1 subjected to the image registration on the body surface, so that the ratio of the projection on the body surface to the actual dimensions of the human body is (0.9-1.1): 1, and a position on the body surface corresponding to the anatomical target on the projected model is an actual projection, on the body surface, of the to-be-located anatomical target.

15. The method of claim 13, wherein the computer data processing component is provided with image enhancement algorithm software inside the computer data processing component, wherein the image enhancement algorithm software is configured to analyze and extract characteristics of points, lines or faces in the gallery 1 and the gallery 2, perform a graphic transformation and a coordinate transformation on the model in the gallery 1, and perform the registration on the model in the gallery 1 and the superficial vein map in the gallery 2.

16. The method of claim 15, wherein the graphic transformation comprising one of: a rigid transformation, an affine transformation, projection transformation, or a bending transformation.

17. The method of claim 1, wherein projecting the model on the body surface where the superficial veins are located comprises projecting the model on the body surface where the superficial veins are located such that the ratio of the projection on the body surface to the actual dimensions of the human body is (0.95-1.05):(0.95-1.05); or printing, by the transparent material, the model according to the size ratio (0.95-1.05):(0.95-1.05) to the human body to obtain the superficial vein mold.

18. A device for locating a human target using superficial vein characteristics, comprising: a vein display device, a brace and a human target matching device, wherein
   the brace comprises a ring-shaped bracket and a plurality of legs connected to the ring-shaped bracket; the vein display device is disposed on the ring-shaped bracket; and the human target matching device is a superficial vein mold or a projector, wherein the superficial vein mold comprises a transparent material on which a vein map and a human target hole are disposed, in a case where the human target matching device is the projector, the projector is connected to the vein display device; and
   the ring-shaped bracket is provided with at least one support ring for supporting the vein display device; and a number of the plurality of legs is at least three, and each of the legs comprises a slip ring and a support rod connected to the slip ring, wherein the slip ring is sleeved on the vein display device.

19. The device of claim 18, wherein a cross-section of a tube of the ring-shaped bracket is non-circular, and a hole of the slip ring is non-circular; or the slip ring is provided with a locking knob for preventing the slip ring from rotating around the ring-shaped bracket.

20. The device of claim 18, wherein the support rod comprises a first support rod and a second support rod rotatably connected to the first support rod, wherein one end of the first support rod is connected to the slip ring, and the other end of the first support rod is rotatably connected to the second support rod through a folding joint; or the support rod is arc-shaped, an end of the support rod is connected to the slip ring, and the other end of at least one support rod is provided with an arc-shaped snap ring, wherein a bottom of the arc-shaped snap ring is a soft structure; or the device for locating the human acupoint according to the superficial vein characteristics further comprises a base, wherein the support rod is inserted into the base.

* * * * *